United States Patent
Abiven

(10) Patent No.: US 10,271,886 B2
(45) Date of Patent: Apr. 30, 2019

(54) PATIENT-SPECIFIC INSTRUMENTATION FOR IMPLANT REVISION SURGERY

(71) Applicant: ZIMMER, INC., Warsaw, IN (US)

(72) Inventor: Jean-Guillaume Abiven, Montreal (CA)

(73) Assignee: ZIMMER, INC., Warsaw, IN (US)

( * ) Notice: Subject to any disclaimer, the term of this patent is extended or adjusted under 35 U.S.C. 154(b) by 535 days.

(21) Appl. No.: 13/948,833

(22) Filed: Jul. 23, 2013

(65) Prior Publication Data
US 2014/0025348 A1     Jan. 23, 2014

Related U.S. Application Data
(60) Provisional application No. 61/674,529, filed on Jul. 23, 2012.

(51) Int. Cl.
*G06F 17/50* (2006.01)
*A61B 17/88* (2006.01)
(Continued)

(52) U.S. Cl.
CPC .......... *A61B 17/8872* (2013.01); *A61B 6/485* (2013.01); *A61B 6/505* (2013.01);
(Continued)

(58) Field of Classification Search
None
See application file for complete search history.

(56) References Cited

U.S. PATENT DOCUMENTS 4,841,975 A   6/1989 Woolson
5,098,383 A   3/1992 Hemmy et al.
(Continued)

FOREIGN PATENT DOCUMENTS

AU   2004293091 A1   6/2005
AU   2004293104 A1   6/2005
(Continued)

OTHER PUBLICATIONS

Trampuz, Andrej, and Werner Zimmerli. "Prosthetic joint infections: update in diagnosis and treatment." Swiss Med Wkly 135. 17-18 (2005): 243-51.*

(Continued)

*Primary Examiner* — Aniss Chad
*Assistant Examiner* — Nithya J. Moll
(74) *Attorney, Agent, or Firm* — Norton Rose Fulbright Canada LLP

(57) ABSTRACT

A system and method for generating a patient specific instrumentation jig model for implant revision comprises an anchor surface identifier to identify anchor surface(s) from a patient specific bone model of a bone requiring implant revision and from data related to an implanted implant on the bone. The anchor surface is in close proximity to the implanted implant. A PSI revision jig model generator generates a jig model using at least the identified anchor surface and a model of a replacement implant, the PSI revision jig model generator outputting a jig model comprising patient specific contact surface(s) corresponding to the identified anchor surface, and at least one tool interface portion positioned and/or oriented relative to the at least one contact surface, the at least one tool interface portion adapted to be interfaced to a tool altering the bone for subsequently installing an implant on the bone.

19 Claims, 2 Drawing Sheets

(51) Int. Cl.
*A61F 2/28* (2006.01)
*A61B 6/00* (2006.01)
*A61B 17/15* (2006.01)
*A61B 17/17* (2006.01)
*A61B 6/03* (2006.01)
*A61F 2/46* (2006.01)
*A61B 17/56* (2006.01)
*A61B 34/10* (2016.01)

(52) U.S. Cl.
CPC .......... *A61B 6/5211* (2013.01); *A61B 17/155* (2013.01); *A61B 17/157* (2013.01); *A61B 17/1764* (2013.01); *A61F 2/28* (2013.01); *G06F 17/50* (2013.01); *A61B 6/032* (2013.01); *A61B 2017/568* (2013.01); *A61B 2034/108* (2016.02); *A61F 2002/4619* (2013.01)

(56) References Cited

U.S. PATENT DOCUMENTS

| | | |
|---|---|---|
| 5,490,854 A | 2/1996 | Fisher et al. |
| 5,768,134 A | 6/1998 | Swaelens et al. |
| 5,769,092 A * | 6/1998 | Williamson, Jr. ........................... A61B 17/8847 128/898 |
| 5,871,018 A | 2/1999 | Delp et al. |
| 5,897,559 A | 4/1999 | Masini |
| 5,916,219 A | 6/1999 | Matsuno et al. |
| 7,357,057 B2 | 4/2008 | Chiang |
| 7,468,075 B2 | 12/2008 | Lang et al. |
| 7,510,557 B1 | 3/2009 | Bonutti |
| 7,534,263 B2 | 5/2009 | Burdulis |
| 7,618,451 B2 | 11/2009 | Berez et al. |
| 7,634,119 B2 | 12/2009 | Tsougarakis et al. |
| 7,717,956 B2 | 5/2010 | Lang |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,806,897 B1 | 10/2010 | Bonutti |
| 7,967,868 B2 | 6/2011 | White et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,070,752 B2 | 12/2011 | Metzger et al. |
| 8,077,950 B2 | 12/2011 | Tsougarakis et al. |
| 8,083,745 B2 | 12/2011 | Lang et al. |
| 8,092,465 B2 | 1/2012 | Metzger et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,133,234 B2 | 3/2012 | Meridew et al. |
| 8,160,345 B2 | 4/2012 | Pavlovskaia et al. |
| 8,175,683 B2 | 5/2012 | Roose |
| 8,221,430 B2 | 7/2012 | Park et al. |
| 8,234,097 B2 | 7/2012 | Steines et al. |
| 8,241,293 B2 | 8/2012 | Stone et al. |
| 8,282,646 B2 | 10/2012 | Schoenefeld et al. |
| 8,298,237 B2 | 10/2012 | Schoenefeld |
| 8,327,519 B2 * | 12/2012 | Linares ................... 219/121.67 |
| 8,337,501 B2 | 12/2012 | Fitz et al. |
| 8,337,507 B2 | 12/2012 | Lang et al. |
| 8,343,218 B2 | 1/2013 | Lang et al. |
| 8,366,771 B2 | 2/2013 | Burdulis et al. |
| 8,377,129 B2 | 2/2013 | Fitz et al. |
| 8,439,926 B2 | 5/2013 | Bojarski et al. |
| 8,460,304 B2 | 6/2013 | Fitz et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski |
| 8,585,708 B2 | 9/2013 | Fitz et al. |
| 8,545,569 B2 | 10/2013 | Fitz et al. |
| 8,551,099 B2 | 10/2013 | Lang |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 2003/0055502 A1 | 3/2003 | Lang et al. |
| 2003/0216669 A1 | 11/2003 | Lang et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2005/0234461 A1 | 10/2005 | Burdulis et al. |
| 2005/0267584 A1 | 12/2005 | Burdulis et al. |
| 2006/0111722 A1 | 5/2006 | Bouadi |
| 2007/0083266 A1 | 4/2007 | Lang |
| 2007/0100462 A1 | 5/2007 | Lang et al. |
| 2007/0156171 A1 | 7/2007 | Lang et al. |
| 2007/0157783 A1 | 7/2007 | Chiang |
| 2007/0198022 A1 | 8/2007 | Lang et al. |
| 2007/0226986 A1 | 10/2007 | Park et al. |
| 2007/0233141 A1 | 10/2007 | Park et al. |
| 2007/0233269 A1 | 10/2007 | Steines et al. |
| 2007/0250169 A1 | 10/2007 | Lang |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0195216 A1 | 8/2008 | Philipp |
| 2008/0243127 A1 | 10/2008 | Lang et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0024131 A1 | 1/2009 | Metzgu et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 * | 6/2009 | Park et al. ...................... 606/88 |
| 2009/0222014 A1 | 9/2009 | Bojarksi et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1 | 10/2009 | White et al. |
| 2009/0270868 A1 * | 10/2009 | Park et al. ...................... 606/87 |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |

(56) References Cited

U.S. PATENT DOCUMENTS

| | | |
|---|---|---|
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarsld et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Matson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0282473 A1* | 11/2011 | Pavlovskaia et al. .......... 700/98 |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1* | 8/2012 | Pavlovskaia et al. .......... 29/428 |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0265496 A1* | 10/2012 | Mahfouz .......................... 703/1 |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |

(56) References Cited

U.S. PATENT DOCUMENTS

| | | |
|---|---|---|
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |

(56) References Cited

FOREIGN PATENT DOCUMENTS

| | | | |
|---|---|---|---|
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SC | 193484 A1 | 10/2013 |
| SG | 173840 A1 | 9/2011 |
| SG | 175229 A1 | 11/2011 |
| SG | 176833 A1 | 1/2012 |
| SG | 178836 A1 | 4/2012 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Taylor et al, "Computer-Integrated Surgery, Technology and Clinical Applications", The MIT Press, Cambridge, MA, London, UK, pp. 451-463.

Hofmann et al, "Natural-Knee II System", Intermedics Orthopedics, Austin, TX, 1995.

\* cited by examiner

PATIENT-SPECIFIC INSTRUMENTATION FOR IMPLANT REVISION SURGERY

CROSS-REFERENCE TO RELATED APPLICATION

The present application claims priority on U.S. Provisional Patent Application No. 61/674,529, filed on Jul. 23, 2012 and incorporated herewith by reference.

FIELD OF THE INVENTION

The present disclosure pertains to patient specific instrumentation (PSI) used in orthopaedic surgery and, more particularly, to PSI used for implant revision.

BACKGROUND OF THE INVENTION

An implant revision process is a process by which an existing implant is removed to be replaced. However, due to the bond between the implant to be removed and the bone, the bone is often damaged during implant revision. As a result, the subsequent positioning and installation of a replacement implant may lack precision due to damaged bone surfaces. For instance, in knee revision surgery, machining of the bone surfaces using conventional cutting blocks may lack precision as conventional bone landmarks used for defining the orientation of the cutting block may be altered or removed during the removal of the implant.

Patient specific instrumentation (hereinafter "PSI") pertains to the creation of instruments that are made specifically for the patient. PSI are typically manufactured from data using imaging to model bone geometry. Therefore, PSI have surfaces that may contact the bone in a predictable way as such contact surfaces are specifically manufactured to match the surface of a bone of a given patient. It would therefore be desirable to use PSI technology in an implant removal process.

SUMMARY OF THE DISCLOSURE

It is an aim of the present disclosure to provide a method for creating a PSI jig for implant revision.

It is a further aim of the present disclosure to provide a system for creating a PSI implant revision jig model.

Therefore, in accordance with the present disclosure, there is provided a method for creating a patient specific instrumentation jig for implant revision, comprising: obtaining a model of at least part of a bone requiring implant revision, the model being physiologically patient specific; obtaining a model of a replacement implant; identifying at least one anchor surface on the bone from the model of the bone and from data related to an implanted implant on the bone, the anchor surface being in close proximity to the implanted implant; and generating a jig model using at least the identified anchor surface and the model of the replacement implant, the jig model comprising at least one patient specific contact surface corresponding to the identified anchor surface for complementary contact, and at least one tool interface portion positioned and/or oriented relative to the at least one contact surface, the at least one tool interface portion adapted to be interfaced with a tool altering the bone for subsequently installing an implant.

Further in accordance with the present disclosure, generating the jig model comprises generating a cut slot as the at least one contact surface.

Still further in accordance with the present disclosure, identifying at least one anchor surface from data related to an implanted implant comprises obtaining a model of the implanted implant on the bone.

Still further in accordance with the present disclosure, obtaining a model of at least part of a bone comprises imaging the part of the bone and the implanted implant on the bone, and generating the model of the part of the bone with the implanted implant.

Still further in accordance with the present disclosure, obtaining a model of at least part of a bone comprises obtaining images of a femur at a knee.

Still further in accordance with the present disclosure, identifying at least one anchor surface comprises identifying at least one of surfaces of an epicondyle and an interior cortex as the at least one anchor surface.

Still further in accordance with the present disclosure, generating the jig model comprises generating at least one cut slot oriented and positioned for at least one predetermined femoral cut plane.

Still further in accordance with the present disclosure, obtaining a model of at least part of a bone comprises obtaining images of a tibia at a knee.

Still further in accordance with the present disclosure, identifying at least one anchor surface comprises identifying at least one of surfaces of medial and lateral aspects of the tibia and of a superior tubercle portion of the tibia as the at least one anchor surface.

Still further in accordance with the present disclosure, generating the jig model comprises generating at least one cut slot oriented and positioned with at least one predetermined tibial cut plane.

Further in accordance with the present disclosure, there is provided a system for generating a patient specific instrumentation jig model for implant revision, comprising: an anchor surface identifier to identify at least one anchor surface from a patient specific bone model of a bone requiring implant revision and from data related to an implanted implant on the bone, the anchor surface being in close proximity to the implanted implant; and a PSI revision jig model generator to generate a jig model using at least the identified anchor surface and a model of a replacement implant, the PSI revision jig model generator outputting a jig model comprising at least one patient specific contact surface corresponding to the identified anchor surface, and at least one tool interface portion positioned and/or oriented relative to the at least one contact surface, the at least one tool interface portion adapted to be interfaced to a tool altering the bone for subsequently installing an implant on the bone.

Further in accordance with the present disclosure, a model generator generates the model of the part of the bone with the implanted implant from images of the part of the bone and the implanted implant on the bone.

Still further in accordance with the present disclosure, an imaging unit images the part of the bone and the implanted implant on the bone.

Still further in accordance with the present disclosure, said data related to an implanted implant is a model of the implanted implant on the bone.

Still further in accordance with the present disclosure, the at least one anchor surface is at least one surface of an epicondyle and an interior cortex of a femur.

Still further in accordance with the present disclosure, the jig model comprises at least one cut slot oriented and positioned for at least one predetermined femoral cut plane.

Still further in accordance with the present disclosure, the at least one anchor surface is at least one surface of medial and lateral aspects of the tibia and of a superior tubercle portion of a tibia.

Still further in accordance with the present disclosure, the jig model comprises at least one cut slot oriented and positioned for at least one predetermined tibial cut plane.

DESCRIPTION OF THE PREFERRED EMBODIMENTS

Figure 1:
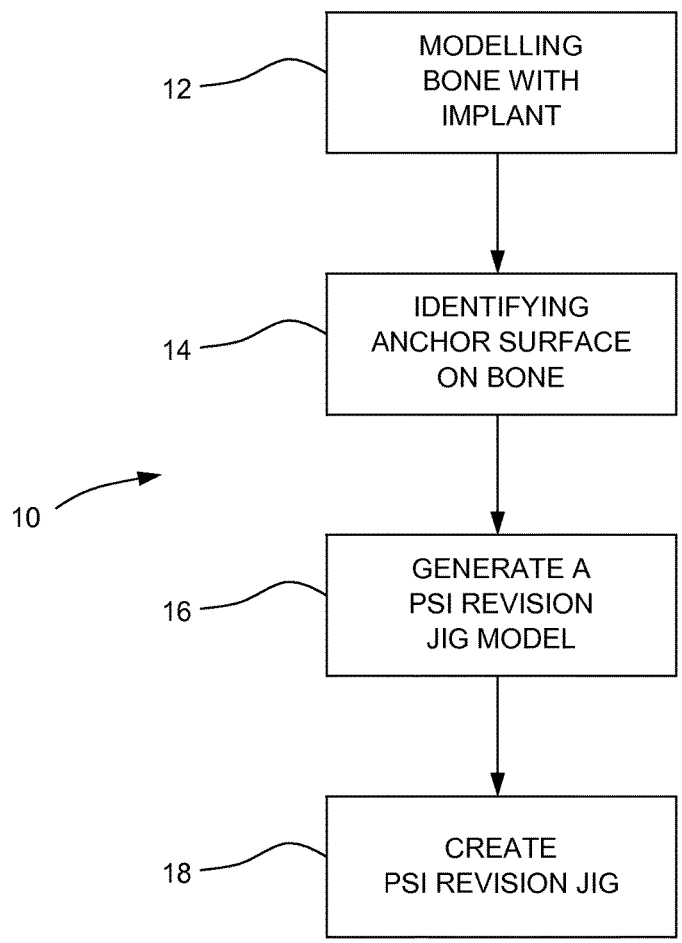
FIG. 1 is a flow chart showing a method for creating a PSI jig for implant revision in accordance with an embodiment of the present disclosure.

Referring to the drawings, and more particularly to FIG. 1, there is illustrated a method 10 for creating patient specific instrumentation (hereinafter PSI) jig for implant revision. For clarity, reference to patient specific in the present application pertains to the creation of negative corresponding surfaces, i.e., a surface that is the negative opposite of a patient bone/cartilage surface, such that the patient specific surface conforms to the patient bone/cartilage surface, by complementary confirming contact. The method is particularly suited to be used in knee revision in which the tibial knee implant, the femoral knee implant or both implants need to be replaced. The method may also be used in other orthopedic implant revision surgery, for instance in shoulder revision surgery.

According to 12, the bone and its implant are modeled. The models may be obtained and/or generated using imaging. The imaging may be done by any appropriate technology such as CT scanning (computerized tomography), fluoroscopy, or like radiography methods, providing suitable resolution of images. The model of the bone comprises a surface geometry of parts of the bone that are exposed despite the presence of the implant and/or the limitations of the imaging. The model of the bone may include a surface geometry of the implant relative to adjacent bone surfaces, and a 3D geometry of the implant, for instance using a 3D model of implant (e.g., from the manufacturer, etc).

The bone modeling may comprise generating a 3D surface of the bone if the bone modeling is not directly performed by the imaging equipment, or if not complete. In the instance in which multiple implants must be replaced (e.g., total knee revision), all bones supporting implants are modeled. Additional structures may be modeled as well, such as cartilage, etc.

According to 14, anchor surfaces are identified on the bone from the model(s) of 12. The anchor surfaces are selected as being sufficiently large to support a PSI jig, and as not being altered by the removal of the implant from the bone. For example, in the case of femoral knee revision, the anchor surfaces may be the epicondyles and the interior cortex. The epicondyles may be used to restore the joint line to set the axial position of the replacement implant. Other parts of the femur may also be used as anchor surfaces.

As another example, in the case of tibial knee implant replacement, the anchor surfaces may be that of the medial and lateral aspects as well as the superior tubercle portion of the tibia. In this case, the medial and lateral aspects may be used to restore the joint line by setting the axial position of the replacement implant. Other parts of the tibia may also be used as anchor surfaces. Similar considerations are taken into account in the case of shoulder surgery. In both cases, the anchor surfaces are in close proximity to the implanted implant as it is in the vicinity of the removed implant that bone alterations will be performed. Although the anchor surface(s) is in close proximity to the removed implant, the anchor surface will not substantially damaged by the removal of the implant.

According to 16, using the anchor surfaces as obtained from the bone model(s) and the geometry of the replacement implant that is known (i.e., obtained from a database, from the manufacturer, generated as a PSI implant, etc), a PSI revision jig model is generated. The jig model will have a contact surface(s) defined to abut against the anchor surface(s) obtained in 14, in a predictable and precise manner. Typically, the PSI revision jig is a cutting block or cutting guide that will allow to cut planes upon which will be anchored the implant. The PSI revision jig model of 16 therefore comprises cutting planes, guides, slots, or any other tooling interface or tool, oriented and/or positioned to allow bone alterations to be formed in a desired location of the bone, relative to the contact surface(s). Thus, PSI revision jig model may also take into consideration any revision planning done by the operator (e.g., surgeon), to therefore allow the removal of sufficient bone material to reproduce desired gaps between cut planes on adjacent bones, etc.

According to 18, once the PSI revision jig model has been generated, the PSI jig may be created. When installing the PSI jig on the bone, the contact surface(s) on the PSI jig is(are) applied against the corresponding anchor surface(s) of step 14. The PSI jig created in 18 may then be used intra-operatively after the implant is removed to allow alterations to be made on the bone. For instance, in the case of total knee revision, jigs are used to perform femoral distal and tibial cuts.

Now that a method for creating a PSI revision jig for implant replacement has been defined, a system is set forth.

Figure 2:
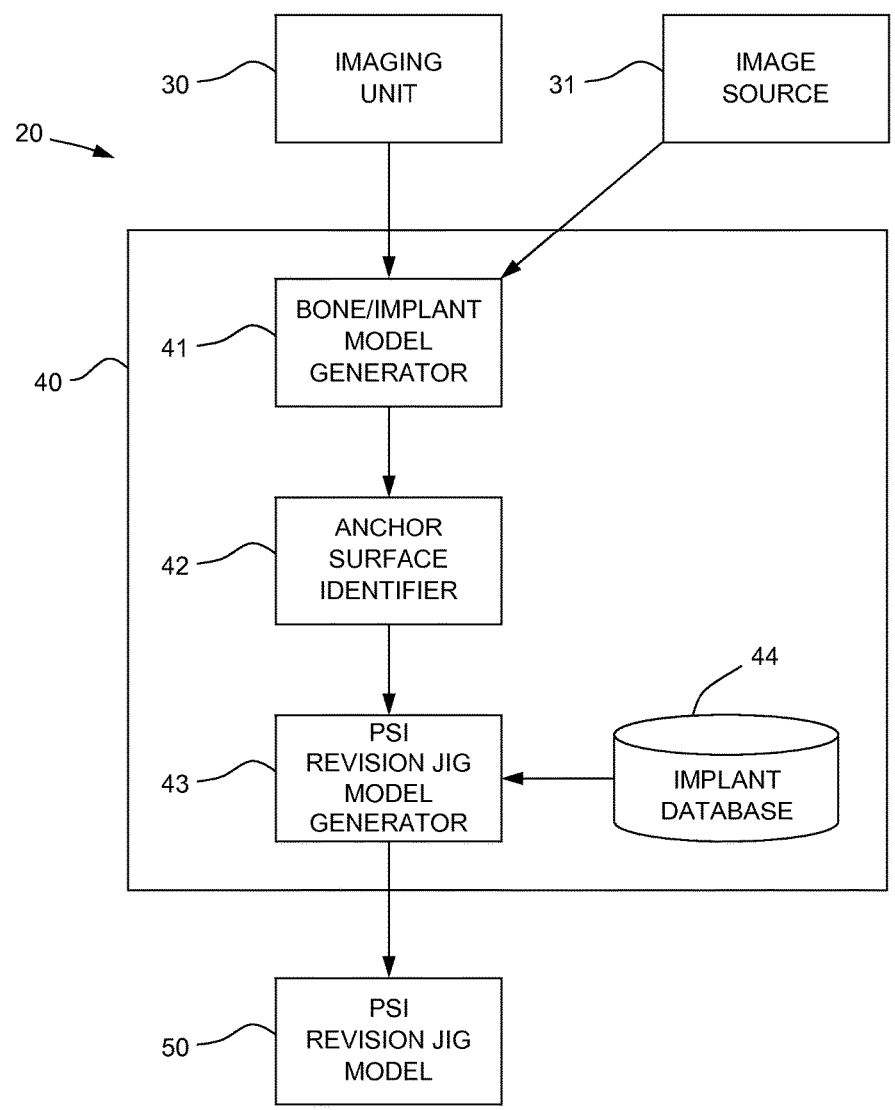
FIG. 2 is a block diagram showing a system for creating a PSI implant revision jig model in accordance with another embodiment of the present disclosure.

A system for the creation of a PSI revision jig model is generally shown at 20 in FIG. 2. The system 20 may comprise an imaging unit 30, such as a CT scan or an X-ray machine, so as to obtain images of the bone and implant. As an alternative, images may be obtained from an image source 31. As an example, a CT scan may be operated remotely from the system 20, whereby the system 20 may simply obtain images and/or processed bone and implant models from the image source 31.

The system 20 comprises a processor unit 40 (e.g., computer, laptop, etc.) that comprises different modules so as to ultimately produce a revision jig model. The processing unit 40 of the system 20 may therefore comprise a bone/implant model generator 41 receiving images from sources 30 or 31 to generate a 3D model of the bone with the implant, prior to implant revision. In accordance with the method 10 of FIG. 1, the 3D model of the bone with implant may comprise data pertaining to the surface geometry of a relevant portion of a bone, including surfaces of the bone that are exposed despite the presence of the implant.

The bone/implant model generator 41 will create the 3D model of the bone and implant that is then used by an anchor surface identifier 42 of the processing unit 40. Alternatively, the anchor surface identifier 42 may use a 3D model provided by the image source 31, provided the model obtained from the image source 31 comprises sufficient data. The anchor surface identifier 42 identifies surfaces on the bone that will substantially not be altered by the removal of the damaged implant. The anchor surface(s) is(are) selected as being sufficiently large to support a PSI jig, and as not obstructing the removal of the implant. For example, reference is made to step 14, in which examples are provided for appropriate anchor surfaces on the femur and the tibia in the case of total knee replacement.

Once the anchor surface(s) is(are) identified, a PSI revision jig model generator 43 will generate a jig model. As in 16 of the method 10, the jig model will have a contact surface(s) defined to abut against the anchor surface(s) identified by the anchor surface identifier 42, in a predictable and precise manner. As the PSI revision jig will support a tool to perform alterations on the bone, the jig model comprises cutting planes, guides, slots, or any other tooling interface or tool, trackers (oriented and/or positioned to allow bone alterations to be formed in a desired location of the bone, relative to the contact surface(s).

Thus, PSI revision jig model generator 43 may also take into consideration any revision planning done by the operator (e.g., surgeon). The PSI revision jig model generator 43 may also take into consideration a geometry of the existing damaged implant, the replacement implant (e.g., obtained from an implant database 44), in addition to the anchor surface(s).

Accordingly, the system 20 outputs a PSI revision jig model 50 that will be used to create the PSI revision jig. The PSI revision jig is then used intra-operatively to resurface bone for subsequent implant installation, as described for method 10 in FIG. 1.

While the methods and systems described above have been described and shown with reference to particular steps performed in a particular order, these steps may be combined, subdivided or reordered to form an equivalent method without departing from the teachings of the present disclosure. Accordingly, the order and grouping of the steps is not a limitation of the present disclosure.

The invention claimed is:

1. A method for creating a patient specific instrumentation (PSI) jig for implant revision, comprising:
    obtaining a model of at least part of a bone requiring removal of an implanted implant being mounted to the bone, the model being physiologically patient specific and being obtained from imaging of the implanted implant as installed on the bone;
    obtaining a model of a replacement implant used to replace the implanted implant on the bone;
    identifying alterations to the bone through the removal of the implanted implant using the model of the bone and data related to the implanted implant;
    identifying at least one anchor surface for the PSI jig on the bone, the anchor surface being in close proximity to the implanted implant, the anchor surface selected for being unaltered through the removal of the implanted implant; and
    generating a jig model using at least the identified anchor surface and the model of the replacement implant, the jig model comprising at least one patient specific contact surface corresponding to the identified anchor surface for complementary contact, and at least one tool interface portion positioned and/or oriented relative to the at least one contact surface, the at least one tool interface portion adapted to be interfaced with a tool altering the bone for subsequently installing the replacement implant after removal of the implanted implant.

2. The method according to claim 1, wherein generating the jig model comprises generating a cut slot on the at least one contact surface.

3. The method according to claim 1, wherein identifying at least one anchor surface from data related to an implanted implant comprises obtaining a model of the implanted implant on the bone.

4. The method according to claim 1, wherein obtaining a model of at least part of a bone comprises imaging the part of the bone and the implanted implant on the bone, and generating the model of the part of the bone with the implanted implant.

5. The method according to claim 1, wherein obtaining a model of at least part of a bone comprises obtaining images of a femur at a knee.

6. The method according to claim 5, wherein identifying at least one anchor surface comprises identifying at least one of surfaces of an epicondyle and an interior cortex as the at least one anchor surface.

7. The method according to claim 6, wherein generating the jig model comprises generating at least one cut slot oriented and positioned for at least one predetermined femoral cut plane.

8. The method according to claim 1, wherein obtaining a model of at least part of a bone comprises obtaining images of a tibia at a knee.

9. The method according to claim 8, wherein identifying at least one anchor surface comprises identifying at least one of surfaces of medial and lateral aspects of the tibia and of a superior tubercle portion of the tibia as the at least one anchor surface.

10. The method according to claim 9, wherein generating the jig model comprises generating at least one cut slot oriented and positioned with at least one predetermined tibial cut plane.

11. A system for generating a patient specific instrumentation (PSI) jig model for implant revision, comprising:
    an anchor surface identifier configured to receive a patient specific bone model of a bone supporting an implanted implant and requiring removal of the implanted implant mounted thereon, the patient specific bone model of the bone obtained from imaging of the implanted implant as installed on the bone, the anchor surface identifier identifying alterations to the bone through the removal of the implanted implant using the patient specific bone model and data related to the implanted implant, and identifying at least one anchor surface for the PSI jig, the anchor surface being in close proximity to the implanted implant, the anchor surface selected for being unaltered through the removal of the implanted implant; and
    a PSI revision jig model generator to generate the PSI jig model using at least the identified anchor surface and a model of a replacement implant used to replace the implanted implant on the bone, the PSI revision jig model generator outputting a jig model comprising at least one patient specific contact surface corresponding to the identified anchor surface, and at least one tool interface portion positioned and/or oriented relative to the at least one contact surface, the at least one tool interface portion adapted to be interfaced to a tool altering the bone for subsequently installing the replacement implant on the bone after removal of the implanted implant.

12. The system according to claim 11, further comprising a model generator for generating the model of the part of the bone with the implanted implant from images of the part of the bone and the implanted implant on the bone.

13. The system according to claim 12, further comprising an imaging unit for imaging the part of the bone and the implanted implant on the bone.

14. The system according to claim 11, wherein said data related to an implanted implant is a model of the implanted implant on the bone.

15. The system according to claim 11, wherein the at least one anchor surface is at least one surface of an epicondyle and an interior cortex of a femur.

16. The system according to claim 15, further comprising the jig model, the jig model comprising at least one cut slot oriented and positioned for at least one predetermined femoral cut plane.

17. The system according to claim 11, wherein the at least one anchor surface is at least one surface of medial and lateral aspects of the tibia and of a superior tubercle portion of a tibia.

18. The system according to claim 17, further comprising the jig model, the jig model comprising at least one cut slot oriented and positioned for at least one predetermined tibial cut plane.

19. A method for creating a patient specific instrumentation (PSI) jig for implant revision, comprising:
obtaining a model of at least part of a bone requiring removal of an implanted implant being mounted to the bone, the model being physiologically patient specific and being obtained from imaging of the implanted implant as installed on the bone;
obtaining a model of a replacement implant used to replace the implanted implant on the bone;
identifying alterations to the bone through the removal of the implanted implant using the model and data related to the implanted implant; and
identifying at least one anchor surface on the bone for anchoring the PSI jig on the bone, the at last one anchor surface being exposed on the model despite a presence of the implanted implant, the anchor surface being in close proximity to the implanted implant, the anchor surface selected for being unaltered through the removal of the implanted implant; and
generating a jig model using at least the identified anchor surface and the model of the replacement implant, the jig model comprising at least one patient specific contact surface corresponding to the identified anchor surface for complementary contact, and at least one tool interface portion positioned and/or oriented relative to the at least one contact surface, the at least one tool interface portion adapted to be interfaced with a tool altering the bone for subsequently installing the replacement implant after removal of the implanted implant.

* * * * *